United States Patent [19]
Smith et al.

[11] Patent Number: 5,563,329
[45] Date of Patent: Oct. 8, 1996

[54] SYSTEM AND METHOD FOR TESTING FLOOR COVERINGS

[75] Inventors: Gary W. H. Smith; Garrick D. S. Smith, both of Columbus, Wis.

[73] Assignee: Simuwear Corporation, Columbus, Wis.

[21] Appl. No.: 305,000

[22] Filed: Sep. 13, 1994

[51] Int. Cl.⁶ ..................................................... G01N 3/56
[52] U.S. Cl. ................................................. 73/7; 73/12.01
[58] Field of Search ........................................ 73/7, 12.01

[56] References Cited

U.S. PATENT DOCUMENTS

| | | | |
|---|---|---|---|
| 2,797,574 | 2/1955 | Rusca et al. | 73/7 |
| 3,516,281 | 12/1968 | Taub | 73/7 |
| 3,641,807 | 2/1972 | Brooks | 73/7 |
| 3,835,697 | 9/1974 | Schneider et al. | 73/7 |
| 3,971,245 | 7/1976 | Crafford et al. | 73/7 |

*Primary Examiner*—Richard Chilcot
*Assistant Examiner*—Max Noori
*Attorney, Agent, or Firm*—Reinhart, Boerner, Van Deuren, Norris & Rieselbach, s.c.

[57] ABSTRACT

A system and method for testing floor coverings provides test data that not only permit meaningful comparisons of various types of floor coverings relative to each other but also permit accurate prediction of how the floor covering samples will perform in actual use. Floor covering testing is provided by repeatedly subjecting a floor covering sample to simulated footfall impacts. The simulated footfall impacts include normal and shear components that are selected based on actual physiological studies of the human gait. The floor covering testing is performed based on the expected pedestrian traffic to be encountered by the floor covering in use. In certain tests, the type of soil expected at the installation site is taken into consideration. The amount of soil retained by particular floor covering samples is measured. Additional tests measure pile retention, in the case of carpets, to predict changes in appearance through usage over time. Other tests measure the ability of a floor covering sample to maintain tension and to provide coefficients of friction consistent with acceptable performance.

28 Claims, 3 Drawing Sheets

SYSTEM AND METHOD FOR TESTING FLOOR COVERINGS

BACKGROUND OF THE INVENTION

This invention relates generally to testing methods for carpets and other floor coverings and, more particularly, to methods of obtaining meaningful comparative data regarding the performance and functional characteristics of such coverings.

The ultimate test of a floor covering's performance is how well it actually performs in service. Such empirical testing is usually impractical, however, in that carpets and other floor coverings can serve for years before serious design flaws or other inadequacies become apparent. Furthermore, conscientious and responsible floor covering manufacturers need to test their products thoroughly before placing them on the market. Allowing an inferior product to reach the marketplace can harm a manufacturers' reputation and reduce its market share. Accordingly, manufacturers cannot afford to use the marketplace itself as a testing or proving ground for their products. Floor covering manufacturers thus have a need for accurate, reliable and effective test procedures and methods in order to obtain meaningful performance data regarding their products.

Floor covering testing is also of importance from a consumer's point of view. Floor coverings not only represent a sizable monetary investment but can affect a consumer's health and well-being as well. Inappropriately selected floor coverings can contribute to falls, aggravate musculo-skeletal disorders and adversely affect indoor air quality. For the purchaser who ultimately has to live with whatever floor covering is purchased and installed, there is too much risk in buying an unproven product. Consumers, too, need access to accurate, reliable and meaningful test data regarding floor coverings.

Because of the impracticality of waiting to see how a particular floor covering performs in actual service, a variety of techniques have been proposed for predicting the performance of particular floor coverings. Typically, the general approach is to accelerate the apparent wear in a floor covering sample. This can be achieved, for example, by placing a floor covering sample in an actual high traffic area or by simulating pedestrian traffic using a machine. Although such approaches have been effective in substantially reducing the time needed to cause noticeable wear in a floor covering sample, neither approach has been totally satisfactory in providing reliable, reproducible and ultimately valuable test information.

A principal difficulty in using actual pedestrian traffic for testing purposes is the lack of uniformity and repeatability in the test conditions. For example, the actual number of footfalls landing on the sample typically is not known with total accuracy. Similarly, ambient conditions, such as temperature and humidity, can vary from day to day or from test site to test site. Finally, the soil conditions might be vastly different between the test site and the site where the floor covering will actually be used. Floor coverings that test well in one part of the country might perform substantially differently at another site where weather conditions are different or where the local geology results in considerably more or less-abrasive soil conditions. Because of such variability in test conditions, it is difficult to make meaningful comparisons among various types of floor coverings. Similarly, acceptable performance at a particular test site does not guarantee similar performance at a different site.

To avoid the problems associated with using actual pedestrian traffic for test purposes, various types of testing machines have been developed. Such machines typically subject a floor covering sample to repetitive impacts or other physical stresses meant to simulate pedestrian traffic. Because the impact repetition rate can be made much higher and sustained much longer than any floor covering is ever likely to encounter in actual use, testing machines greatly reduce the time needed to run a useful test. Similarly, testing machines make it possible to duplicate test conditions and thereby obtain at least some comparative data from among many test samples. Nevertheless, prior testing machines and test methods were not without deficiencies.

One principal deficiency of prior testing machines and methods was that the impacts applied to the floor covering sample did not accurately simulate actual footfall forces. Thus, although some comparative data could be acquired regarding the performance of samples relative to each other, little absolute information could be acquired regarding how well a particular product would perform in actual use. In other words, a test could tell whether one carpet would last longer than another, but could not tell whether either carpet would last for a specified period of time.

Another deficiency of prior testing machines and methods was that the tests typically took place under artificial conditions. For example, carpet samples were often tested without regard to the sometimes substantial tension actual carpets are placed under when installed. Similarly, the type of subfloor and padding over which the actual carpet would be installed was sometimes ignored in testing. Finally, prior testing did not take into account the type, nature and amount of soil carpets absorb when subjected to actual pedestrian traffic. All these factors affect carpet performance and should be considered if meaningful test data are to be generated.

Still another drawback of prior testing machines and methods was that the machines and methods lacked flexibility. Generally, the machines were configured to perform one type of test only and could not be readily adapted to perform other tests. If additional test information was needed, it was necessary to acquire a completely different machine.

SUMMARY OF THE INVENTION

The invention provides a method of testing a floor covering and finishes applied to flooring materials including the steps of providing a sample of the floor covering, subjecting the sample of floor covering to simulated installed conditions and thereafter subjecting the floor covering sample to repeated simulated footfall impacts. The footfall impacts include a predetermined normal force component and a predetermined shear force component.

The invention also provides a method of selecting floor coverings so as to match the best selected floor covering to actual conditions at the site where the selected floor covering will be installed. Initially, at least one performance criterion to be satisfied by the floor covering to be installed at the installation site is identified. Pedestrian traffic is surveyed at the installation site to determine an average footfall force representative of the typical impact forces generated by pedestrians at the installation site. The average footfall force is resolved into a normal force component and sheer force component. A plurality of different floor covering samples are subjected to repeated simulated footfall impacts wherein the simulated footfall impacts have normal force component and sheer force components substantially equal to the normal force components and the sheer force component of the average footfall force. The floor covering samples are then compared with respect to the performance criterion to determine which of the floor covering samples best satisfies the performance criterion.

BRIEF DESCRIPTION OF THE DRAWINGS

The features of the present invention that are believed to be novel are set forth with particularity in the appended claims. The invention, together with the further objects and advantages thereof, may best be understood by reference to the following description taken in conjunction with the accompanying drawings, wherein like reference numerals identify like elements, and wherein:

DESCRIPTION OF THE PREFERRED EMBODIMENT

Figure 5:
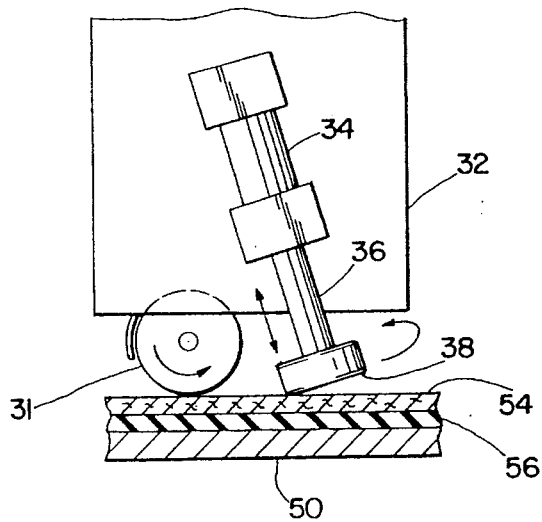
FIG. 5 is a detailed view of a pneumatic impactor cylinder included in the floor covering tester shown in FIG. 1.

Applicant's co-pending patent application Ser. No. 08/093,865 filed Jul. 19, 1993 and entitled "Floor Covering Foot Impact Simulator," (the specification of which is incorporated by reference herein), shows and describes one form of floor covering test machine 20 that is particularly well suited to implementing the floor covering test methods herein disclosed. This machine 20, which is shown generally in FIGS. 1–5, supports a sample of carpeting or other floor covering 54 and repeatedly subjects the sample 54 to controlled impacts that simulate actual footfall impacts. The controlled impacts are delivered to the floor covering specimen at an angle (the "shear" angle α, FIG. 5) so that the resulting impact force has both a perpendicular or normal component and a tangential or shear component. The impact forces, which in the embodiment illustrated are delivered by means of a pneumatic cylinder 34 (the "impactor cylinder"), can be varied in both magnitude and direction. In particular, the shear angle by which the pneumatic cylinder deviates from the perpendicular or normal direction can be adjusted. By increasing this angle, the shear component of the impact force can be increased. Additionally, by varying the applied air pressure, the overall magnitudes of the shear and normal force components can be varied. Preferably, a heel member 38 that simulates footwear is attached to the lower end of the impactor cylinder 34 and makes the actual contact with the floor covering specimen 54 during each impact.

The testing machine further includes a specimen table 26 on which the floor covering sample 54 to be tested is mounted. Means are included for providing relative movement between the floor covering sample 54 and the impactor cylinder 34. In the illustrated embodiment, the floor covering sample or test specimen 54 is mounted on the specimen table 26, and the specimen table 26 is mounted for independent movement along two orthogonal horizontal axes below the impactor 34. In addition, the specimen table 26 can be rotated around a vertical axis beneath the impactor. By appropriately controlling movement of the specimen table along the two linear axes and around the vertical rotational axis, the impacts of the impact cylinder 34 onto the floor covering sample 54 can be distributed in a variety of predetermined patterns. It will be appreciated that, alternatively, the specimen table 24 can be held stationary and the impactor cylinder 34 moved.

Figure 1:
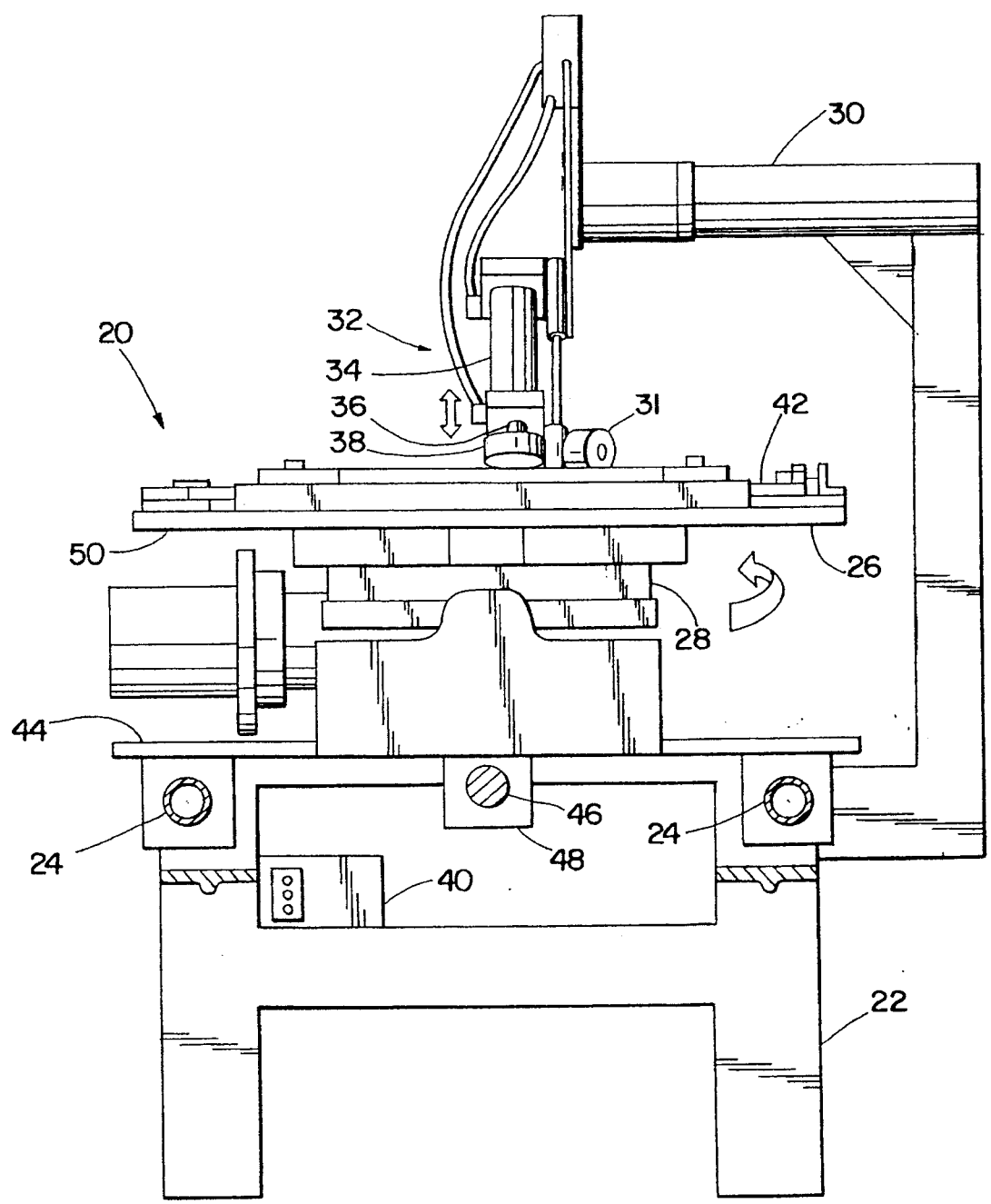
FIG. 1 is a front elevational view of one form of floor covering tester useful in performing the various tests herein disclosed.
Figure 2:
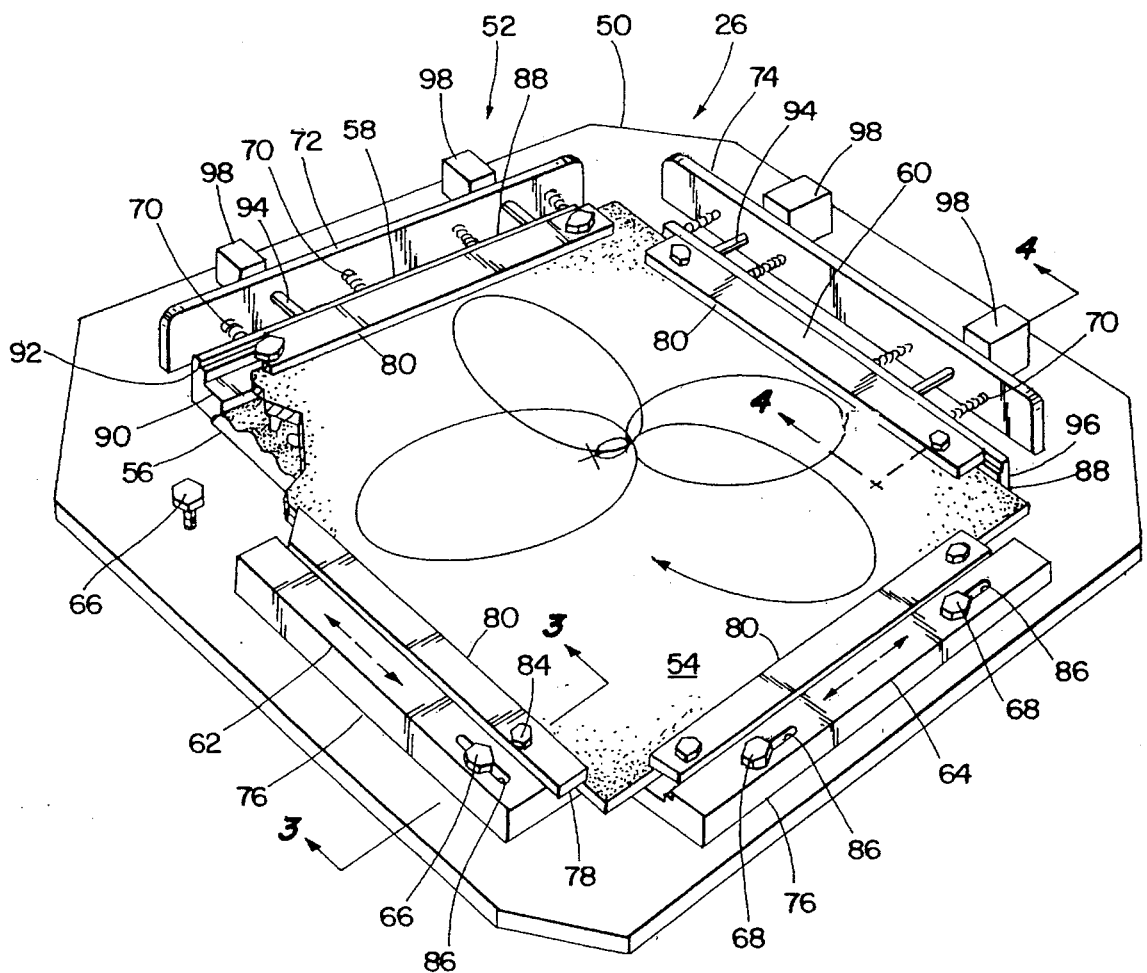
FIG. 2 is an isometric view, partially broken away, of a specimen table included in the floor covering tester shown in FIG. 1.
Figure 3:
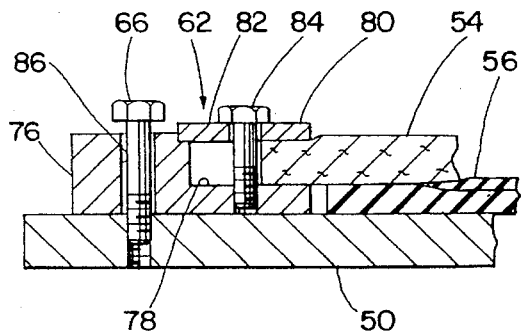
FIG. 3 is a cross-sectional view of the floor covering tester shown in FIG. 2 taken along line 3—3.
Figure 4:
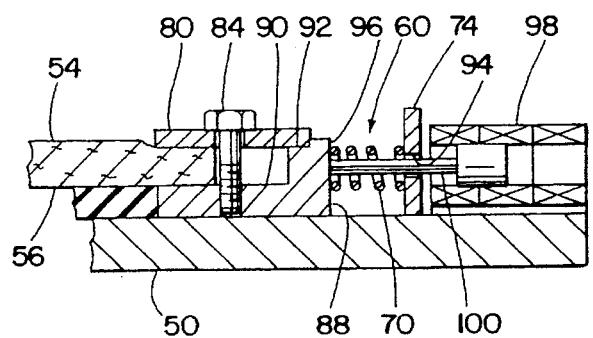
FIG. 4 is a cross-sectional view of the floor covering tester shown in FIG. 2 taken along line 4—4.

The specimen table 26 shown in FIG. 2 is arranged to support the floor covering sample in a manner that simulates actual installed conditions. To this end, the floor covering sample or specimen 54, which is square in the illustrated embodiment, is grasped along each of its edges under tension by means of opposed clamps 80. Two of the clamps, engaging adjacent edges of the sample, are fixed to the specimen table 26. The opposing clamps, which engage the remaining edges, are movable relative to the specimen table 26 and can be tensioned by means of springs 70 to simulate an actual carpet installation. Additionally, a cushion underlay 56, such as a section of carpet pad or backing, can be placed under the test sample 54.

By appropriately utilizing various of the capabilities provided by the machine, various test protocols can be developed to provide meaningful comparative test data among various types of floor coverings. In contrast to prior test methods that provided an empirical comparison among various floor covering samples, the test protocols described herein provide meaningful performance data that not only permit comparisons of various floor coverings relative to each other but that are repeatable and permit accurate predictions of actual floor covering performance in actual installations. Various possible testing protocols are described below.

PERFORMANCE TESTING

In the performance testing protocol, the goal is to determine how well a particular floor covering sample will perform in actual usage. To this end, the test conditions are set up to duplicate as closely as possible the actual conditions under which the floor covering sample will be called upon to perform. An important step in such testing is determining accurately what those conditions are.

Physiological studies suggest that the human gait changes with age and that the nature of footfall forces generated by pedestrians varies among various age groups. In particular, older adults tend to take shorter strides than younger adults and contact the floor with less shear force than do younger adults. Both groups develop footfall forces that are markedly different from those of young children who weigh less but who tend to run more. Thus, the footfall forces likely to be encountered in a nursing home can differ markedly from those to be expected in an elementary school or daycare center. Accordingly, a principal step of a preferred testing protocol is to identify the character of the expected pedestrian traffic and to identify such expected use conditions as (1) the expected weight and age of the pedestrians, (2) the expected shear angle of the footfalls likely to fall on the floor covering, (3) the magnitudes of the expected normal and shear components of the expected footfall forces and (4) the nature of the footwear likely to be worn by the expected pedestrians. After these data are identified, the testing machine can be set up so as to simulate the actual expected pedestrian traffic.

To further simulate actual installed conditions, the floor covering sample to be tested should be installed as it will be in actual use. Specifically, a backing or pad, if used, should also be installed on the specimen table below the sample to be tested and the sample to be tested should be placed under the same tension it will experience when in actual use. Ideally, the actual make and model of the pad to be used in the proposed installation should also be used in the test. If extreme conditions of temperature or humidity are anticipated, such conditions can be duplicated at the testing site. The heel member attached to the impactor cylinder is preferably selected to match the anticipated footwear of the expected pedestrians. By setting up the test conditions in this manner and subjecting various floor covering samples to repeated, simulated footfall forces, the floor covering best suited for the particular application can be identified and selected.

As explained in detail in co-pending application Ser. No. 08/093,965, the floor covering sample under test and the impactor cylinder are preferably moved relative to each other so as to create a predetermined pattern of desired footfall impact densities in desired zones of the floor covering sample. Preferably, the predetermined pattern provides a gradient between a maximum density of footfall impacts at one area of the floor covering sample and a minimum density of footfall impacts at another area of the floor covering sample. In this manner, it is possible to predict with accuracy how the physical characteristics and appearance of the floor covering sample will change with increasing pedestrian traffic.

PILE THICKNESS

In the pile thickness testing protocol, the objective is to determine how a particular carpet will wear when subjected to continued pedestrian traffic. In this test, the thickness of the floor covering sample is measured before and after being subjected to simulated footfall forces. Preferably, the simulated footfall forces are set up (by adjusting normal and shear force component magnitudes) to simulate the expected footfall forces of the anticipated pedestrian traffic. The footfall forces are preferably applied to the sample under test so as to create a gradient of footfall impact densities in different zones of the sample. The pile thickness in the various zones is measured to determine how the pile thickness changes with use. The pile thickness test is of value when the retention of pile thickness is an important criterion in selecting a floor covering. This is particularly significant when the appearance of a carpet is of importance.

DIMENSIONAL STABILITY

In the dimensional stability testing protocol, the question of primary interest is how the length and width of a stretched carpet varies with continued usage and wear. Residential carpets are typically placed under considerable tension when first installed. This tension causes the length and width of the carpet to change as the carpet stretches. The degree to which a carpet requires stretching, and the ability of a carpet to maintain a desired tension, can be important criteria in selecting carpeting for most applications. The dimensional stability testing protocol provides quantifiable data indicative of a particular carpet sample's ability to resist stretching under tension or to maintain stable tension while in use.

In the dimensional stability protocol, the test specimen is preferably first conditioned under climate-controlled conditions to ensure uniform and repeatable moisture content. For example, the test specimen can be placed for 24 hours in a chamber containing air at a temperature of 20° C. and a relative humidity of 65%. Following conditioning, the test specimen is installed on the specimen table over a new cushion of the type that will be used in the proposed installation. The test specimen is then placed under a predetermined measured spring tension (e.g., 120 pounds) in length and the same tension in width to simulate being power stretched in a field installation. The initial stretch is measured before beginning the test by measuring the length and width of the unstretched test specimen at rest and comparing these dimensions to the length and width of the test specimen after stretching but before impacting. The testing machine is then actuated to repeatedly drive the impactor cylinder(s) into contact with the test specimen. At designated intervals Coy time or unit impact measure) the machine is stopped to measure and record further changes in the length and width of the test specimen. After a given period of time (e.g., eight hours) the test is considered complete and a final record of the overall dimensional change is made. The dimensional stability test thereby provides an hourly record of how well the test specimen maintains its dimensions under actual use.

By way of example, the machine can be adjusted to provide 120 simulated footfall impacts per minute or 7,200 impact per hour per cylinder. Thus, an eight hour test typically records approximately 57,600 impacts per cylinder. The addition of one or more cylinder accellerates results without changing the method of production.

As previously noted, the magnitudes of the normal and shear components of the simulated footfall forces can be adjusted and are preferably selected to match the anticipated footfall forces generated by the expected pedestrian traffic.

SOIL CONDITIONING

The soil conditioning testing protocol tests the propensity of a particular carpet to release entrapped soil. Despite various efforts to vacuum, steam clean, water extract or otherwise chemically clean carpets, experience shows that no cleaning method is 100% effective and that some soil is always retained within the carpet. The retained soil that cannot be removed, can degrade the appearance of the carpet and can ultimately contribute to the physical breakdown and mechanical failure of the carpet. The soil conditioning testing protocol measures carpet performance characteristics where such cleanliness considerations are of importance. The soil testing protocol also permits the preparation of floor covering specimens having repeatable, known and controlled quantities of soil to produce accurate and meaningful comparison of various floor coverings and cleaning machines, cleaning chemicals, cleaning processes, and techniques.

In the soil conditioning testing protocol, a test specimen is first vacuum cleaned on both its face and back and then dried and weighed. The test specimen is then conditioned under climate-controlled conditions to create moisture equilibrium at a specified temperature. The specimen is removed and weighed. It is next installed on the specimen table of the testing machine.

After the test specimen is installed on the testing machine, a predetermined quantity of a previously prepared standard soil is distributed over a predetermined surface area of the test specimen. The test specimen is then subjected to a predetermined number of simulated footfall impacts after which the specimen is thoroughly vacuum cleaned. The process is repeated until a predetermined overall quantity of the test soil is applied to the specimen and the specimen is subjected to a predetermined total number of impacts. The specimen is then removed from the machine, allowed to regain equilibrium under controlled climatic conditions and then weighed.

Following soil conditioning, the specimen is placed in a drying chamber for a period of time sufficient to ensure the temperature and relative humidity within the specimen is below that of the climate control chamber. The specimen is then removed and weighed before placing it in the climate control chamber which is maintained at 20° C. and 65% relative humidity and there allowed to reach equilibrium. It is then removed from the climate controlled chamber and weighed. Next, the specimen is chemically cleaned using a wet spray detergent with wet vacuum pickup. On line filters within the vacuum line entrap loose fibers and larger components of the soil which are not able to pass through the filter. The pattern of wet extraction application is manual but is conducted in a precise and repeating pattern to ensure the specimen is cleaned uniformly. Captured loose fiber is dried, weighed and added back to the starting weight as an adjustment.

The cleaned specimen is returned to the drying chamber and held until the temperature and humidity are below that of the climate control chamber. The specimen is then removed from the drying chamber and weighed. The specimen is then placed in the climate control chamber and allowed to reach equilibrium within the chamber. The specimen is then removed and weighed to determine the amount of soil remaining in the specimen following chemically cleaning. The end result of the process reveals the amount of soil remaining with the specimen by weight measure.

In selecting the appropriate test soil, it is preferable to utilize components (a) that are likely to be encountered in actual usage, (b) that are representative of the soil conditions likely to be encountered at a particular, proposed installation site, and (c) that can be reproduced with consistency. One preferred form of test soil comprises an oil component and one or more dry powder material components. The oil component can comprise, for example, a household cooking oil consisting of vegetable and canola oil such as "Wesson" oil produced by Hunt-Wesson, Inc. of Fullerton, Calif. The dry materials can consist of bentonite clay, potting soil, washed silica, gypsum and charcoal. One preferred formulation of test soil consists of the following weight percentages of listed ingredients:

| | |
|---|---|
| Bentonite Clay | 44% |
| Potting Soil | 17% |
| Washed Silica | 22% |
| Gypsum | 11% |
| Charcoal | 1% |
| Oil | 5% |

It will be appreciated that other soil compositions can be formulated to match conditions dictated by local geography or specialized use conditions. Preferably the components are mixed for at least two hours in a small, sealed, laboratory mixer.

INDOOR AIR QUALITY

Air quality monitoring sensors can be used to measure particulate materials scuffed from the surface of a test carpet. By locating such devices within the vicinity of the machine (preferably eighteen inches above the tested specimen surface) particulate residue generated by the surface impacting of soiled carpet can be measured. Bio-contaminants can also be monitored using detectors which can gather and measure such air borne particles.

Biochemical contaminants, fungi, and bacteria can be monitored for activity using soil conditioned specimens that have been prepared using a laboratory developed soil and by conditioning the test specimen to be sterile before or after applying said soil or contaminants.

STATIC/DYNAMIC COEFFICIENT OF FRICTION TESTING

It has been shown that static and dynamic coefficient of friction (COF) values for friction pairs containing one or both compressible materials do not behave linearly with normal force as do COF values of incompressible materials. Therefore, it is beneficial to measure static and dynamic COF values for compressible flooring materials utilizing normal and shear forces representative of those of a human. By performing minor modifications to the aforementioned processes, it is possible to measure both static and dynamic coefficient of friction (COF) values for a particular combination of specimen and heel materials utilizing forces representative of those applied by a human. These modifications consist of incorporating sensors to detect and measure the applied normal and shear forces, and establishing the necessary mechanical and electrical controls, and data acquisition equipment.

In the COF testing protocol, a test specimen is installed on the testing machine and the selected heel material is mounted to the lower end of the striking cylinder. Force sensor readings are taken continually for the duration of the test. The respective COF values can be determined as follows:

Static COF—The heel material is pressed against the test specimen by the striking cylinder with constant force representative of that applied by a human. A force is then applied to the specimen in a horizontal direction opposed to the shear force induced by the heel. The force is increased until the heel "slides" on the specimen. The highest force sensor reading recorded during the test divided by the applied normal force yields the static COF for the material pair.

Dynamic COF—The procedure for the Static COF test is performed until the heel "slides" on the specimen at a preselected and controlled velocity. The steady force sensor reading recorded during the controlled "sliding" divided by the applied normal force yields the dynamic COF for the material pair. A test specimen can be measured before and after impact testing to measure change of COF properties.

Although it is anticipated that the floor covering testing protocols described herein will find greatest use in connection with carpeting, it will be appreciated that the testing protocols can also be used effectively to test other forms of floor materials and floor finishes. For example, various forms of resilient flooring, i.e., tile ceramic or wood floor coverings can be tested advantageously. Similarly, the testing of various coatings (e.g., varnishes, etc.) applied to a non-carpet floor covering can also be tested, particularly with respect to such characteristics as wear, appearance and coefficient of friction. Accordingly, the testing protocols herein described should not be viewed as being limited only to carpets.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

I claim:

1. A method of testing a floor covering comprising the steps of:
   providing a sample of the floor covering;
   subjecting the sample of floor covering to simulated installed conditions; and
   thereafter subjecting the floor covering sample to repeated simulated footfall impacts, said footfall impacts being applied to the floor covering sample along a nonperpendicular angle relative to the floor covering sample so as thereby to include a predetermined normal force component and a predetermined shear force component.

2. A method as defined in claim 1 further comprising the step of distributing said simulated footfall impacts over the floor covering sample in a predetermined pattern so as to achieve desired footfall impact densities in desired zones of the floor covering sample.

3. A method as defined in claim 2 wherein said predetermined pattern provides a gradient between a maximum density of footfall impacts at one area of the floor covering sample and a minimum density of footfall impacts at another area of the floor covering sample.

4. A method as defined in claim 3 wherein the floor covering sample is held relatively stationary and the footfall impacts are delivered at multiple locations to generate said predetermined pattern.

5. A method as defined in claim 3 wherein the footfall impacts are delivered at a single location and the floor covering sample is moved to generate said predetermined pattern.

6. A method as defined in claim 1 wherein the floor covering sample comprises carpet having a pile thickness and wherein said step of subjecting the sample to simulated installed conditions comprises the steps of positioning the sample over a cushion underlay and applying opposing forces at opposite edges of the sample to place the sample under tension.

7. A method as defined in claim 6 further comprising the step of measuring the pile thickness of the sample while subjecting the sample to said footfall impacts to determine the change in pile thickness of the sample with the number of footfall impacts.

8. A method as defined in claim 6 further comprising the step of measuring changes in the thickness of the cushion underlay while subjecting the sample to said footfall impacts to determine the change in pad thickness, stiffness and support with the number of footfall impacts.

9. A method as defined in claim 6 wherein said opposing forces are adjusted to achieve a predetermined desired tension in the sample.

10. A method as defined in claim 9 further comprising the step of monitoring the tension in the sample while subjecting the sample to said footfall impacts to generate data indicative of the change in said tension with the number of footfall impacts.

11. A method as defined in claim 9 further comprising the step of subjecting the sample to said footfall impacts until said tension in the sample decreases from a known initial value to a predetermined final value.

12. A method as defined in claim 9 further comprising the step of measuring changes in the dimensions of the sample while subjecting the sample to said footfall impacts to determine the dimensional stability of the sample.

13. A method of testing a floor covering comprising the steps of:
    providing a sample of the floor covering;
    subjecting the sample of floor covering to simulated installed conditions;
    thereafter subjecting the floor covering sample to repeated simulated footfall impacts, said footfall impacts including a predetermined normal force component and a predetermined shear force component;
    weighing and climate conditioning the sample prior to subjecting the sample to said footfall impacts;
    applying a predetermined quantity of soil to the sample prior to subjecting the sample to said footfall impacts;
    vacuum cleaning at designated intervals during application and at conclusion to remove loose particles of soil;
    cleaning the sample after subjecting the sample to said footfall impacts to remove loose soil from the sample and gather loose fiber; and
    weighing the sample following said cleaning to determine the proportion of soil retained by the sample.

14. A method as defined in claim 13 wherein said step of cleaning the sample includes the step of vacuuming the sample.

15. A method as defined in claim 13 wherein said step of cleaning the sample comprises the step of applying a chemical cleaning agent.

16. A method as defined in claim 13 wherein said soil comprises a mixture of predetermined proportions of preselected ingredients.

17. A method as defined in claim 16 wherein said preselected ingredients comprise oil and one or more dry powder materials.

18. A method as defined in claim 17 wherein said dry powder materials comprise one or more of bentonite clay, potting soil, washed silica, gypsum and charcoal.

19. A method of testing a floor covering comprising the steps of:
    providing a sample of the floor covering;
    initially dry conditioning the sample by subjecting the sample to known temperature conditions for a predetermined period prior to testing;
    subjecting the sample of floor covering to simulated installed conditions; and
    thereafter subjecting the floor covering sample to repeated simulated footfall impacts, said footfall impacts including a predetermined normal force component and a predetermined shear force component.

20. A method as defined in claim 1 wherein said predetermined normal force and said predetermined shear force components are adjusted to mimic actual pedestrian traffic.

21. A method of selecting floor coverings so as best to match the selected floor covering to actual conditions at the site where the selected floor covering will be installed, said method comprising the steps of:
    identifying at least one performance criterion to be satisfied by the floor covering to be installed at the installation site;
    surveying pedestrian traffic at the installation site to determine an average footfall force representative of the typical impact forces generated by pedestrians at the installation site;
    resolving said average footfall force into a normal force component and a shear force component;
    subjecting a plurality of different floor covering samples to repeated simulated footfall impacts, said simulated footfall impacts having normal force component and shear force component substantially equal to said normal force components and said shear force components of said average footfall force; and comparing said floor covering samples with respect to said performance criterion to determine which of said floor covering samples best satisfies said performance criterion.

22. A method as defined in claim 21 wherein said performance criterion comprises the ability of the floor covering to resist apparent wear.

23. A method as defined in claim 21 wherein said performance criterion comprises the ability of the floor covering to maintain dimensional stability.

24. A method as defined in claim 21 wherein said performance criterion comprises the ability of the floor covering to retain soil of a known type and amount when exposed to soil and measured forces as applied to the floor covering.

25. A method as defined in claim 21 wherein said performance criterion comprises the ability of the floor covering to release a percentage of said soil when exposed to wet extraction chemical cleaning.

26. A method as defined in claim 21 wherein said survey of pedestrian traffic takes into account the expected age and physical characteristics of the pedestrians and wherein said normal force and shear force components and said simulated footfall impacts are selected in accordance with the age and physical characteristics of the pedestrians.

27. A method as defined in claim 21 wherein said survey of pedestrian traffic takes into account the heel configurations of footwear worn by the pedestrians and wherein said simulated footfall impacts are delivered to the floor covering sample using simulated heel configurations so that said simulated footfall impacts substantially mimic the actual footfall impacts of the pedestrians.

28. A method as defined in claim 21 wherein said performance criterion is the ability of the floor covering to maintain a desired coefficient of friction over a range of anticipated pedestrian gaits and footfall forces.

* * * * *